US008802037B2

(12) United States Patent
Blouin et al.

(10) Patent No.: US 8,802,037 B2
(45) **Date of Patent: *Aug. 12, 2014**

(54) SAMPLE WELL STRIP

(75) Inventors: Matthew R. Blouin, Townsend, MA (US); Robert R. Fisette, Norwood, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 653 days.

This patent is subject to a terminal disclaimer.

(21) Appl. No.: 13/039,972

(22) Filed: Mar. 3, 2011

(65) Prior Publication Data

US 2011/0152129 A1 Jun. 23, 2011

Related U.S. Application Data

(63) Continuation of application No. 12/755,870, filed on Apr. 7, 2010, now Pat. No. 7,927,876, which is a continuation of application No. 10/007,031, filed on Nov. 8, 2001, now abandoned.

(51) Int. Cl.
*C12M 1/18* (2006.01)

(52) U.S. Cl.
USPC ........ 422/560; 422/562; 422/566; 435/288.4; 435/305.2; 436/47

(58) Field of Classification Search
USPC .......... 422/560, 562, 566; 436/47; 435/288.4, 435/305.2
See application file for complete search history.

(56) References Cited

U.S. PATENT DOCUMENTS

| | | | |
|---|---|---|---|
| 1,643,883 | A | 9/1927 | Fife |
| 3,703,336 | A | 11/1972 | Rosse et al. |
| 3,713,985 | A | 1/1973 | Astle |
| 3,775,595 | A | 11/1973 | Rosse et al. |
| 3,971,106 | A | 7/1976 | Chambers |
| 3,973,915 | A | 8/1976 | Raffaele et al. |
| 4,022,579 | A | 5/1977 | Revillet et al. |
| 4,178,345 | A | 12/1979 | Terk |
| D257,175 | S | 9/1980 | Terk |
| D257,394 | S | 10/1980 | Reichler |
| 4,226,531 | A | 10/1980 | Tiffany et al. |
| D260,428 | S | 8/1981 | Fekete |
| 4,313,735 | A | 2/1982 | Yamashita et al. |
| D265,124 | S | 6/1982 | Terk |
| D266,589 | S | 10/1982 | Gilford et al. |
| 4,432,643 | A | 2/1984 | Koizumi et al. |
| D280,131 | S | 8/1985 | Takasugi |

(Continued)

FOREIGN PATENT DOCUMENTS

| | | | |
|---|---|---|---|
| EP | 0902548 | A2 | 3/1999 |
| EP | 0965385 | A2 | 12/1999 |

(Continued)

OTHER PUBLICATIONS

International Search Report for International Application No. PCT/US02/33941 mailed Apr. 25, 2003.

(Continued)

*Primary Examiner* — Lyle Alexander
(74) *Attorney, Agent, or Firm* — Burns & Levinson LLP

(57) ABSTRACT

A multiple cuvette strip comprises a plurality of wells and a reversible interlocking device. The well strips can be reversibly interlocked to other well strips to form a sample holder system. One embodiment of a well strip comprises a flange and a slot to form a reversible interlocking device.

6 Claims, 11 Drawing Sheets

(56) References Cited

U.S. PATENT DOCUMENTS

| | | | |
|---|---|---|---|
| D282,005 | S | 12/1985 | Kayhko |
| 4,582,684 | A | 4/1986 | Vogel et al. |
| 4,777,141 | A | 10/1988 | Calzi et al. |
| 4,778,763 | A | 10/1988 | Makiguchi |
| 4,787,744 | A | 11/1988 | Hissung |
| 4,877,659 | A | 10/1989 | Vince |
| 4,895,706 | A | 1/1990 | Root et al. |
| 4,929,426 | A | 5/1990 | Bodai et al. |
| 4,933,147 | A | 6/1990 | Hollar et al. |
| 5,084,246 | A | 1/1992 | Lyman et al. |
| 5,092,672 | A | 3/1992 | Vanderwerf |
| 5,098,663 | A | 3/1992 | Berthold et al. |
| D327,743 | S | 7/1992 | Frenkel et al. |
| 5,164,318 | A | 11/1992 | Sato et al. |
| D335,348 | S | 5/1993 | Frenkel et al. |
| 5,233,506 | A | 8/1993 | Semenik et al. |
| 5,266,268 | A | 11/1993 | Antocci et al. |
| 5,285,907 | A | 2/1994 | Franchere et al. |
| 5,358,691 | A | 10/1994 | Clark et al. |
| 5,360,597 | A | 11/1994 | Jakubowicz et al. |
| 5,376,313 | A | 12/1994 | Kanewske, III et al. |
| 5,441,891 | A | 8/1995 | Burkovich et al. |
| 5,456,883 | A | 10/1995 | Burkovich et al. |
| 5,470,536 | A | 11/1995 | Jarvimaki |
| 5,518,693 | A | 5/1996 | Tomasso et al. |
| 5,522,255 | A | 6/1996 | Neel et al. |
| 5,536,664 | A | 7/1996 | Switalski et al. |
| 5,567,387 | A | 10/1996 | Versluys et al. |
| 5,567,617 | A | 10/1996 | Caprio et al. |
| 5,575,046 | A | 11/1996 | Rourke |
| D382,347 | S | 8/1997 | Grubb |
| 5,665,558 | A | 9/1997 | Frame et al. |
| 5,735,387 | A | 4/1998 | Polaniec et al. |
| 5,902,548 | A | 5/1999 | Watts et al. |
| D413,391 | S | 8/1999 | Lapeus et al. |
| D413,677 | S | 9/1999 | Dumitrescu et al. |
| 5,948,363 | A | 9/1999 | Gaillard |
| D416,330 | S | 11/1999 | Brown |
| D481,133 | S | 10/2003 | Blouin et al. |

FOREIGN PATENT DOCUMENTS

| | | |
|---|---|---|
| FR | 627277 | 9/1927 |
| JP | 09187434 | 4/1998 |
| JP | 09340584 | 6/1999 |

OTHER PUBLICATIONS

Extended European Search Report for European Application No. 10164712 issued on Jan. 20, 2011.

SAMPLE WELL STRIP

CROSS REFERENCE TO RELATED APPLICATION

The application is a continuation patent application of U.S. Ser. No. 12/755,870, filed on Apr. 7,2010, now U.S. Pat. No. 7,927,876, which is a continuation application of and claiming priority to and the benefit of a U.S. Ser. No. 10/007,031 filled on Nov. 8, 2001, now abandoned the entire contents of which are incorporated herein by reference.

TECHNICAL FIELD

The present invention relates generally to sample wells for holding samples to be analyzed in an automated sample analyzer, and, more particularly to sample wells for holding body fluid samples for analysis in an automated medical sample analyzer for medical diagnostic test procedures.

BACKGROUND

A sample well strip has a plurality of sample wells which are not in fluid communication with each other, but which are physically connected to each other and typically arranged in a linear array. The sample well strip is typically used for holding samples, such as aliquots of a reaction mixture, environmental samples, blood, urine or fractions of samples thereof, in instruments, such as automated sample analyzers, for use in medical diagnostic test procedures.

A goal of medical laboratories is to enhance laboratory efficiency by analyzing as many samples as possible in a given time period, while at the same time minimizing the number of interactions between laboratory personnel, the samples, and sample analyzers. Sample well strips have been developed that allow multiple samples to be loaded into an automated sample analyzer all at once. Generally, however, each sample well strip is individually loaded, well strip-by-well strip, and manually introduced into the automated sample analyzer in a position ready to receive the test sample. Thus, the number of sample well strips that can be loaded onto the sample analyzer, and the number of samples that can be analyzed per unit time, is limited by the number of well strips that can be arranged, typically side-by-side, on the loading tray of the automated sample analyzer.

Therefore, it would be desirable to provide a sample well strip comprising a plurality of sample wells that increases the number of samples that are analyzed per unit time and that minimizes the interactions between laboratory personnel and individual sample well strips. The goal of this invention is to enhance the efficiency of the automated sample analyzer's performance and capacity by a sample well strip that increases the number of well strips that can be loaded onto the analyzer at any one time.

SUMMARY OF THE INVENTION

In general, the advantages of the present invention provide sample well strips that increase the number of samples that can be analyzed by a sample analyzer within a unit of time and reduce the number of interactions between laboratory personnel and the individual well strips.

In one aspect, the invention relates to a sample holder system having a first and at least a second well strip having a plurality of wells and an interlocking device disposed on the well strips. The interlocking device reversibly engages the first well strip with the second well strip. In one embodiment, the interlocking device has a first engagement piece positioned on the first well strip and a second engagement piece positioned on the second well strip. The first and second engagement pieces reversibly interlock to form a sample holder system.

In another embodiment, the first engagement piece is positioned near the first end of the first well strip and the second engagement piece is positioned near the second end of the second well strip. In another embodiment, the first engagement piece is positioned on a first side wall of the first well strip and the second engagement piece is positioned on a second side wall of a second well strip. In this embodiment, for example, the second engagement piece is positioned at the second end of the first well strip and the first engagement piece is positioned at the second end of the second well strip. In another embodiment of the invention, the first well strip and at least the second well strip are substantially similar.

In one embodiment of the invention, the first engagement piece includes a flange and the second engagement piece includes a slot. Alternatively, the second engagement piece includes a slot and a slit. In one embodiment, the first engagement piece positioned at the first end of the first well strip has a flange and the second engagement piece positioned at the first end of the second well strip has a slot, or, alternatively, a slot and a slit. The interlocking device according to the invention includes a first engagement piece and a second engagement piece.

In another aspect, the invention relates to a first well strip including a plurality of wells, a first engagement piece, and a second engagement piece. The first engagement piece and second engagement piece cooperate to reversibly attach a first well strip and a second well strip.

In another embodiment of this aspect of the invention, the first well strip includes a first engagement piece substantially positioned near a first end of the first well strip and a second engagement piece substantially positioned near a second end of the well strip. In yet another embodiment of this aspect of the invention, the first engagement piece is positioned on a first side wall and the second engagement piece is positioned on a second side wall of the well strip. In a further embodiment, the first engagement piece is a flange and the second engagement piece is a slot, or alternatively, the second engagement piece is a slot and a slit.

In another aspect, the invention relates to a method for increasing the load capacity of an automated sample analyzer. The method according to the invention includes the steps of interlocking a first well strip with at least a second well strip to form a sample holder system and loading a plurality of sample holder systems onto the automated sample analyzer. In one embodiment, the method further includes the steps of detaching a first well strip from the sample holder system by disengaging the first well strip from the second well strip, moving the first well strip, and analyzing the samples in the wells of the first well strip. The plurality of well strips are interlocked by slidably moving the first well strip horizontally relative to at least a second well strip to engage the first and second well strips.

In one embodiment according to this aspect of the invention, the sample held by a well of a well strip is a body fluid, for example, blood, urine, plasma, or serum. The sample can be analyzed in the well of a well strip for a coagulation disorder, electrolyte concentration or to determine the presence or concentration of a drug.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

DETAILED DESCRIPTION

Each of the embodiments of the invention described below have the following common features: a well strip comprising a plurality of sample wells, each well dimensioned to hold a sample, and each well strip reversibly attachable to at least one other well strip to form a sample holder system.

Figure 1:
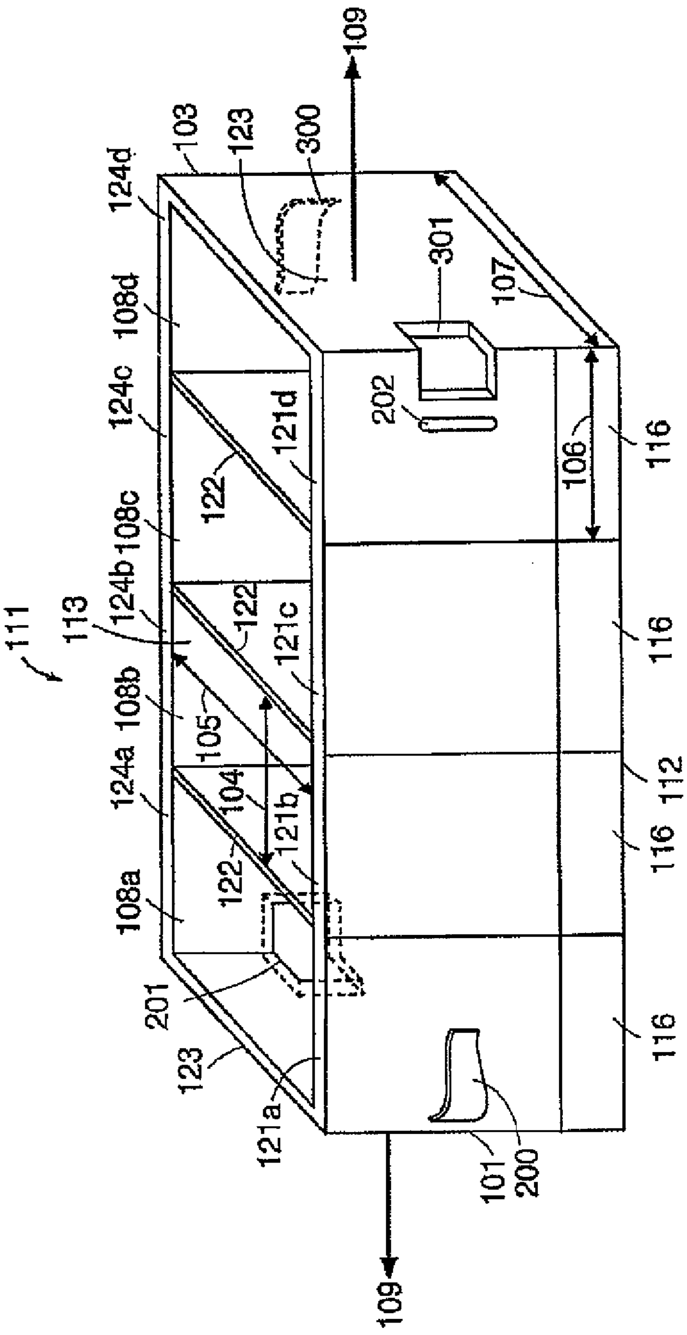
FIG. 1 is a side perspective view of a well strip with four sample wells.

Referring to FIG. 1, in general, according to the invention, a sample well strip 111 has a plurality of wells 108*a*, 108*b*, 108*c*, 108*d*, generally 108 extending from a first end wall 101 of the well strip 111 to a second end wall 103 of the well strip. For example, as illustrated in FIG. 1, in one embodiment, the sample well strip 111 has four wells 108. In a particularly preferred embodiment of the invention, shown in FIG. 2, the well strip 111 is approximately 50-100 mm in length, preferably 66 mm in length, approximately 5-15 mm in width, preferably 9 mm in width, and approximately 12-24 mm in height, preferably 18 mm in height from the well base 112 to the top 113 of the well. The sample well strip 111 is manufactured from materials which are chemically and optically suitable, for example but not limited to, polystyrene, acrylic, or TPX (polyolefin).

The sample wells 108 in a well strip 111 are typically used for holding one of a variety of test samples, such as aliquots of a reaction mixture, an environmental sample, blood, urine, joint fluid, cerebrospinal fluid, and other body fluids or fractions thereof for use in chemical assays, diagnostic test procedures, drug testing, and other assays. For example, blood, serum, or plasma samples held in sample wells 108 are analyzed in sample wells 108 to determine, for example, the concentration of analytes such as glucose, lactate, electrolytes, enzymes, in the sample, or for analysis of coagulation disorders. Fluids other than body fluids can also be analyzed in sample wells 108. For example, drinking water placed in sample wells 108 can be analyzed for purity or contamination.

A test sample placed in sample well 108, according to the invention, can be analyzed in various instruments, such as automated sample analyzers for in vitro diagnostic analysis. Examples of such automated analyzers are manufactured by Instrumentation Laboratory Company, (Lexington, Mass.).

Figure 2:
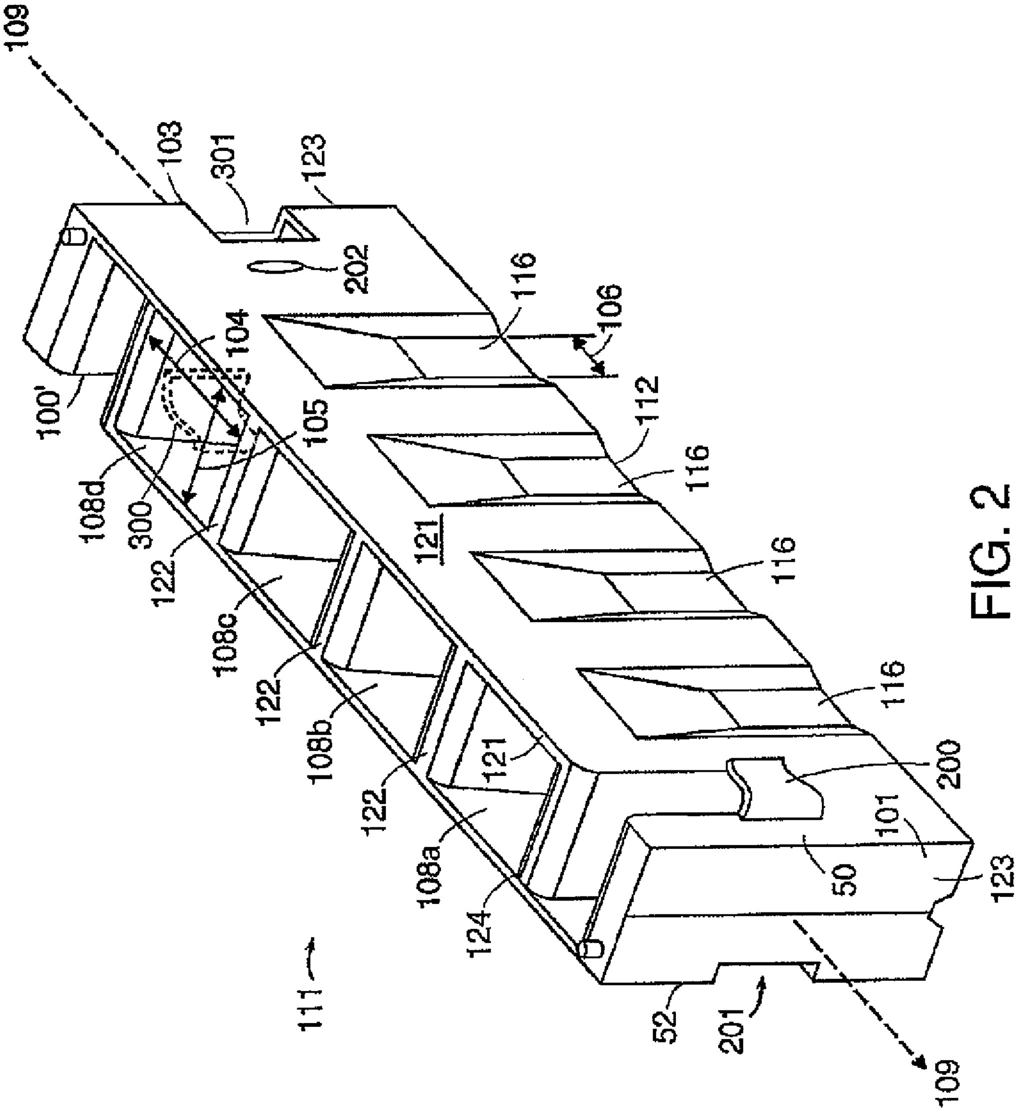
FIG. 2 is a perspective view of a preferred embodiment of a well strip.

With continued reference to FIG. 1 and with reference to FIG. 2, each sample well 108 of the well strip 111 is adjacent to at least one other well 108 to form an array of wells from a first end wall 101 to a second end wall 103 along the longitudinal axis 109 of the well strip 111. The number of sample wells 108 in a well strip 111 may vary. For example, a well strip 111 can have anywhere from 2 to 100 wells 108.

Figure 3A:
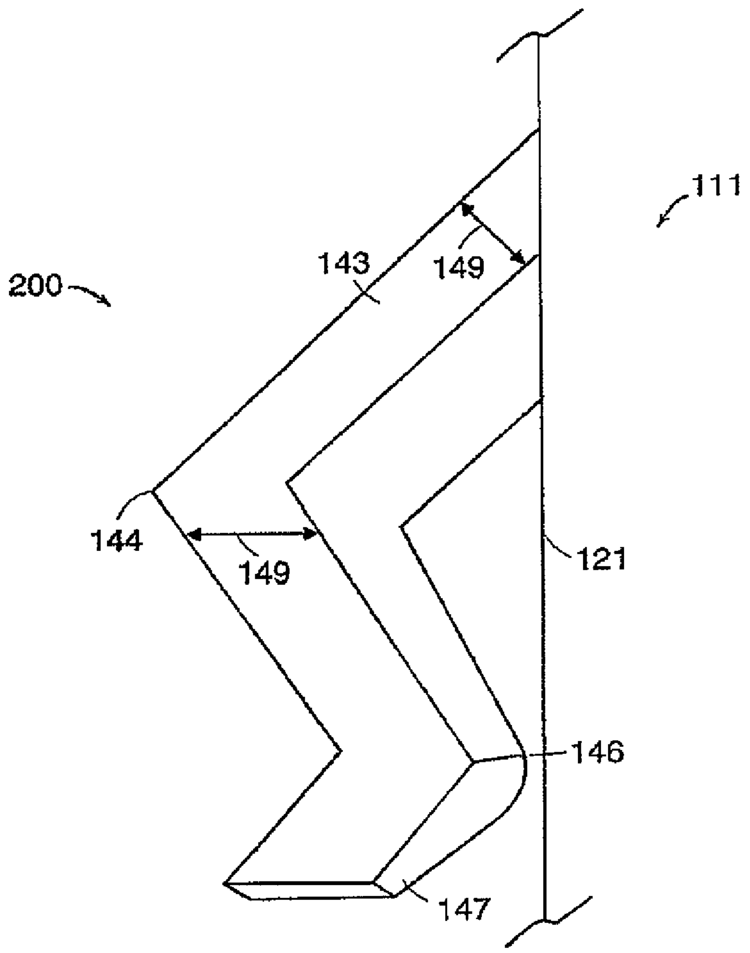
FIG. 3A is a top view of a first engagement piece flange.
Figure 3C:
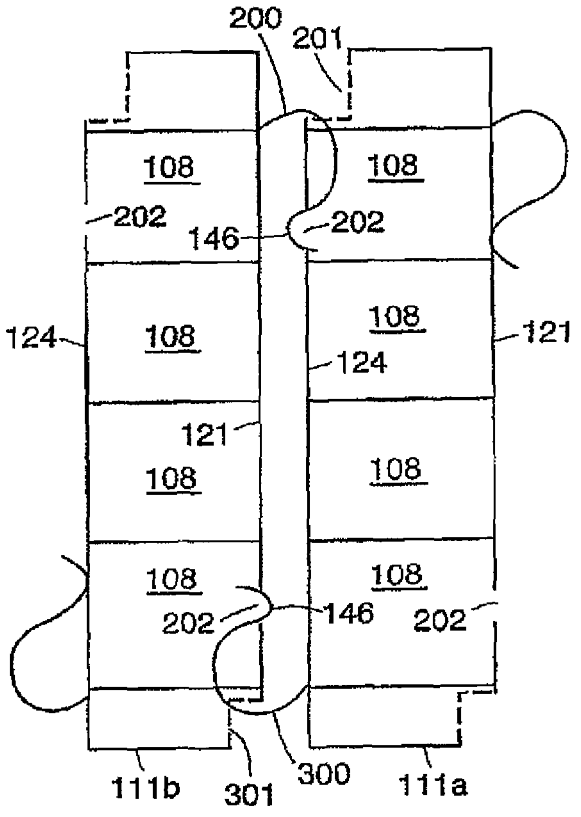
FIG. 3C is a top view of two reversibly engaged well strips.
Figure 4:
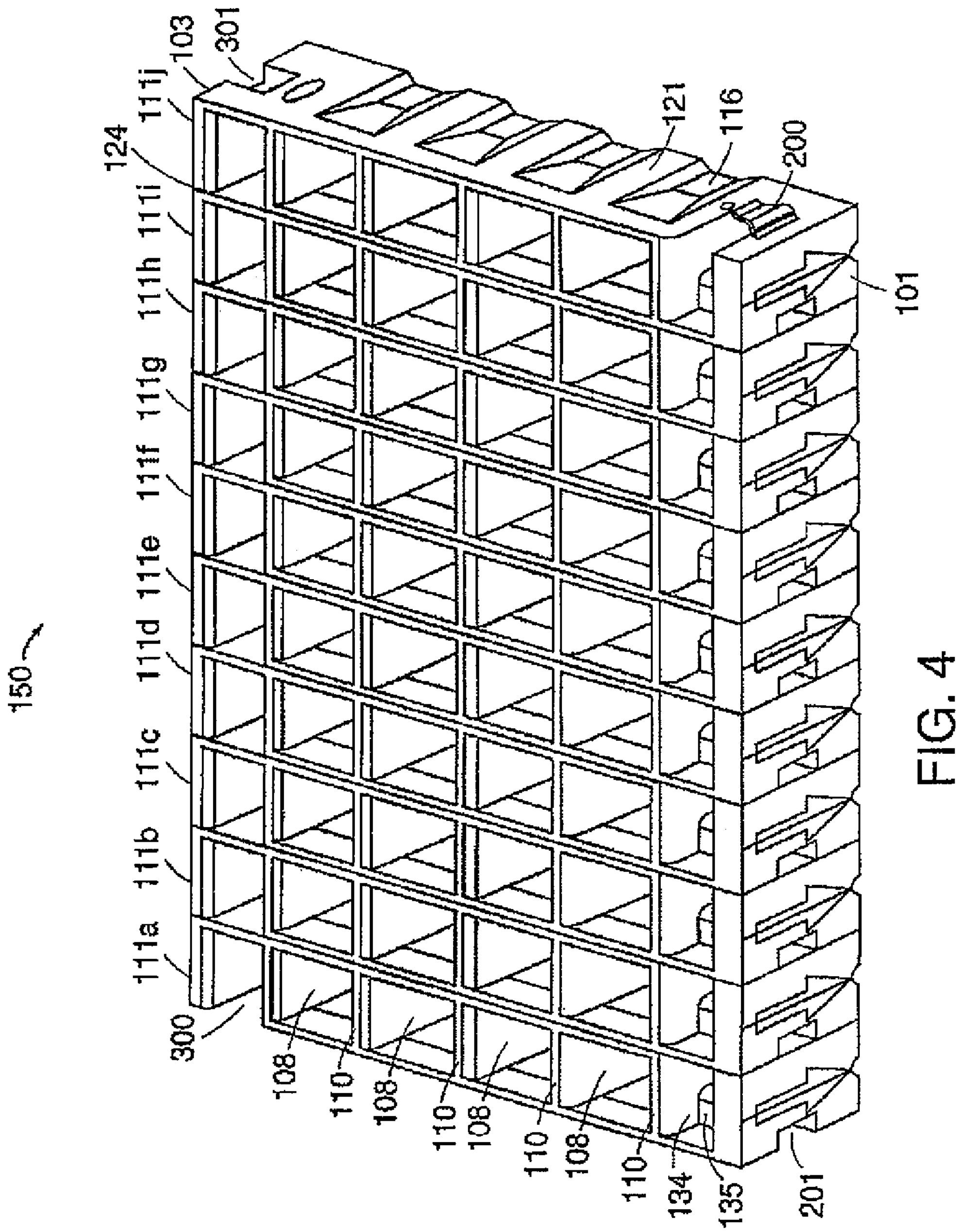
FIG. 4 is a perspective view of a sample holder system comprising a plurality of well strips.

In another aspect of the invention, a sample well strip 111 comprises one or more first engagement pieces, generally 200, such as a flange or a peg, located on a first side wall 121 of the sample well strip 111, shown in FIG. 2, and one or more second engagement pieces, generally 201, such as a slot, shown in shadow in FIG. 2, located on the second side wall 124 of the strip 111, the second side wall being opposite to the first side wall. In a particular embodiment, first side wall 121 and second side wall 124 of a sample well strip 111 are parallel to each other (also see FIG. 3C). When two such sample well strips 111 are placed with the first side wall 121 of a first well strip 111 abutting the second wall 124 of a second well strip 111, the first engagement piece 200 of the first well strip 111 reversibly engages the second engagement piece 201 of the second well strip 111. Thus, the first engagement piece 200 of a first well strip in reversibly interlocks with the second engagement piece 201 of a second well strip 111. The combination of the first engagement piece 200 of one well strip 111 with the second engagement piece 201 of a second well strip 111 comprises a reversible interlocking device. As shown in FIG. 4, when one or more well strips 111 are interlocked, the side walls 121 and 124 of the well strips 111 are parallel, the first end 101 of each well strip is aligned with the first end 101 of each other well strip 111, and the second end 103 of each well strip is aligned with the second end 103 of each other well strip 111.

In other embodiments (not shown) of this aspect of the invention, the reversible interlocking device may include a first engagement piece 200 such as hook, and a second engagement piece 201, such as an eye. Other combinations of the first engagement piece 200 and second engagement piece 201 include but are not limited to, respectively, a hook and a hook, peg and a hole, the two components of a dovetail joint, and various types of first and second adhesive surfaces, such as chemical or fabric adhesives. In a particular embodiment, the first engagement piece and the second engagement piece interlock, i.e., the first engagement piece engages the second engagement piece and temporarily locks in place without permanently deforming the first or the second engagement piece. The first and second engagement pieces are separable following interlocking of the first and second engagement pieces without permanently deforming either the first or second engagement piece.

In a particular embodiment, the first engagement piece 200 and the second engagement piece 201 are reversibly interlocked. A first well strip 111*a* is interlocked with a second well strip 111*b* by engaging the first engagement piece 200 of the first well strip 111*a* with the second engagement piece 201 of a second well strip 111*b*. The second well strip 111*b* may be interlocked with a third well strip 111*c* by engaging the first engagement piece 200 of the second well strip 111*b* with the second engagement piece 201 of a third well strip 111*c*, and so on. In other embodiments, the second engagement piece 201 of the first well strip 111*a* interlocks with the first engagement piece 200 of the second well strip 111*b*, and so on. The location of the first engagement piece 200 and the second engagement piece 201 on either the first, second, third, or more well strips 111, is not important as long as at least one first engagement piece 200 on a well strip 111, can interlock with at least one second engagement piece 201 on an adjacent well strip 111. Well strips 111 that are interlocked via the interlocking device engaging a first engagement piece 200 and a second engagement piece 201 are detached from each other by disengaging the first and second engagement pieces.

In a particular embodiment, the reversible interlocking device includes a clip-like flange first engagement piece 200 and a complementary slot second engagement piece 201. Flange 200, illustrated in FIG. 3A, comprises a cantilevered arm 143 that is attached at the fixed end of the arm 143 to the first side wall 121 or the second side wall 124 (not shown) near one end of the well strip 111 (also see FIG. 2). The opposite end 147 of cantilevered arm 143 is free, i.e., unattached to a side wall of well strip 111. Flange 200 has a first bend at elbow 144 closest to the attachment point of flange arm 143 to the side wall of the well strip 111. The elbow 144 is distanced 1.0-2.0 mm, preferably 1.75 mm from the side wall of the well strip 111. The flange arm 143 is 4-6 mm, preferably 5.20 mm, at the widest dimension of the flange arm 143 indicated by arrow 149 in FIG. 3A. A second bend is positioned at elbow 146, near the free end 147 of the flange arm 143. The outside portion of the bend of the second elbow 146 touches or nearly touches the side wall of well strip 111. Flange arm 143 flexes at its point of attachment to the side wall of well strip 111.

Figure 3B:
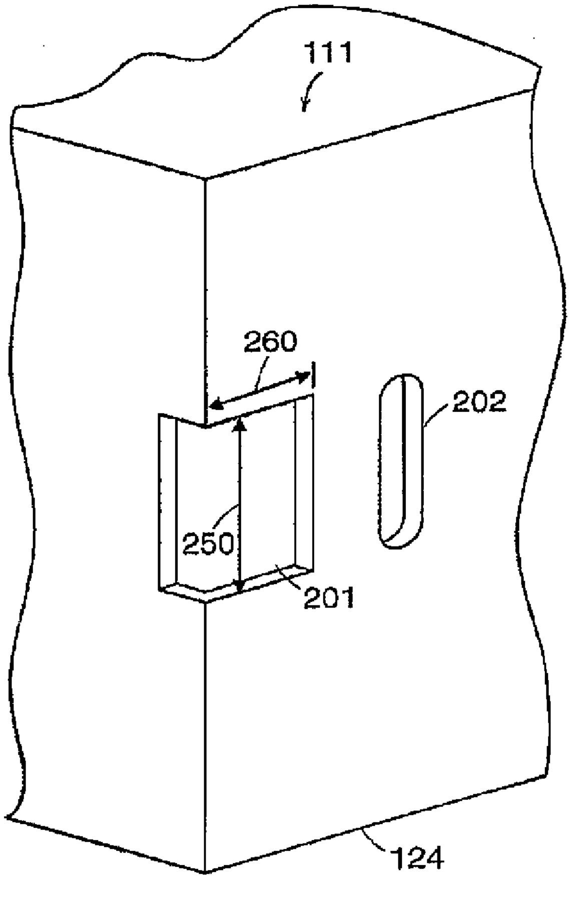
FIG. 3B is a side view of a second engagement piece slot.

A second engagement piece, comprising a slot 201, illustrated in FIG. 3B, is dimensioned to substantially fit the first engagement piece 200 of the reversible interlocking device and is positioned near or preferably at one end of well strip 111 (see FIG. 2). In a particularly preferred embodiment, slot 201 is 5-6 mm, preferably 5.25 mm in height indicated by arrow 250 and 2.5-3.5 mm, preferably 3.0 mm wide, indicated by arrow 260 in FIG. 3B.

In a particular embodiment of a reversible interlocking device, the first engagement piece comprises a flange and the second engagement piece comprises a slot. The second engagement piece 201 may further include a slit 202. As illustrated in FIGS. 2 and 3*b*, slit 202 is a vertically oriented, elongated hole through wall 121 or wall 124 positioned 2-5 mm from slot 201. As shown in FIG. 3C, viewed schematically from the top of well strips 111*a* and 111*b*, with flange 200 engaged in slot 201, the curved portion 146 of the free end 147 of the cantilevered flange 200 is seated "home" and registers in slit 202. When flange 200 is seated in slit 202, the tension in flange arm 143 is relaxed and the interlocking device is reversibly locked.

In a particular embodiment of the invention, illustrated in FIG. 2, a well strip 111 with four wells 108*a*, 108*b*, 108*c*, 108*d* includes a first engagement piece 200 on the first side wall 121 of well strip 111 near one end wall 101 of the strip, and a second engagement piece 201 located on the second side wall 124 of the well strip 111 at the same end 101 of the well strip 111. Another first engagement piece 300 shown in shadow in FIG. 2, is located on the second side wall 124 of the well strip 111 at the opposite end wall 103 of the strip 111, and a second engagement piece 301 is located on the first wall 121 of the well strip 111 at the end wall 103 of the strip 111 on the side wall 121 opposite the first engagement piece 300.

A particular embodiment of the invention shown in FIGS. 1 and 2, is a well strip 111 with flange 200 on the wall opposite slot 201 and slit 202 of the well strip 111 at the first end 101, and flange 300 on the wall opposite to the slot 301 and the slit 202 located at the second end 103. Thus, a well strip 111 having this configuration is reversibly engageable with any other well strip 111 having an identical configuration, to form a sample holder system 150 illustrated in FIG. 4.

Other embodiments of the invention include sample well strips 111 having a first engagement piece 200 on the first end 101 of first side wall 121 of the sample well strip 111, and another first engagement piece 300 on the second end 103 of the first side wall 121 of the sample well strip 111. Alternatively, in another embodiment, first engagement piece 200 and second engagement piece 201 are on the same or opposite side walls of the sample well strip 111 and located anywhere along the longitudinal axis 109 of the sample well strip 111 as long as at least one first engagement piece 200 of a first sample well strip 111 reversibly interlocks with at least one second engagement piece 201 of a second sample well strip 111.

A sample holder system 150, illustrated in FIG. 4, is formed by interlocking two or more sample well strips 111 together, for example, sample well strip 111*a* and sample well strip 111*b*. In one embodiment of the invention, interlocking is accomplished by sliding the flange 200 on the first side wall 121 near the first end 101 of the first sample well strip ilia into the slot 201 on the second side wall 124 near the first end 101 of the second sample well strip 111*b*, and sliding the flange 300 on the second side wall 124 near the second end 103 of the second sample well strip 111*b* into the slot 301 on the first side wall 121 near the second end 103 of the first sample well strip 111*a*. The two interlocked sample well strips ilia and 111*b* are separated by sliding the flanges of each well strip out of the slots of each well strip 111 to unlock the two sample well strips 111*a* and 111*b*.

Using the same interlocking technique, any number of well strips 111 can be interlocked to each other to form a sample holder system 150 as shown in FIG. 4. For example, a sample holder system 150 may include anywhere from 2 to 100, preferably 10 well strips 111*a*-111*j*. The size of the sample holder system 150 is determined by the number of well strips 111 that are interlocked. An advantage of the reversible interlocking system described herein is that this configuration allows any number of well strips 111 to be interlocked to form a sample holder system 150.

Figure 5:
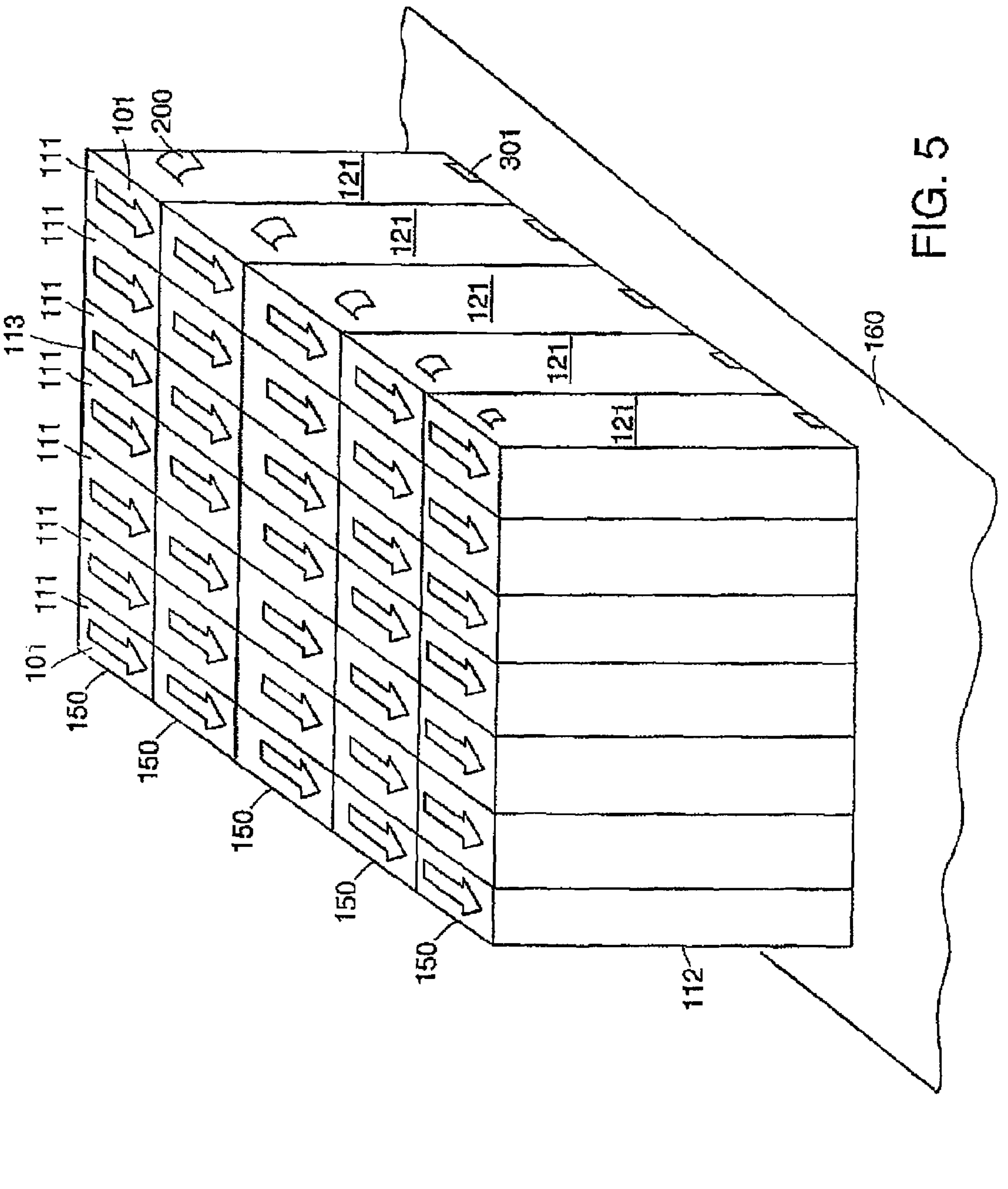
FIG. 5 is a perspective view of a plurality of sample holder systems in a vertical side-by-side arrangement.

The sample holder system 150, shown in FIG. 4, may be stacked side-by-side with a plurality of sample holder systems 150. For example, each sample holder system 150 may be arranged in a vertical orientation, i.e., with end 101, end 103, first wall 121, or second wall 124 resting on conveyor belt 160, as shown in FIG. 5. A series of sample holder systems 150 can be oriented in this manner and stacked side-by-side on a conveyor belt 160 of an automated sample analyzer instrument. In this orientation, a greater number of well strips 111 can be loaded onto a conveyor belt 160 per unit area than sample holder systems 150 arranged in a horizontal orientation, i.e., with the bottom 112 or top 113 of well strip 111 resting on conveyor belt 160. Each well strip 111 of sample holder system 150 is separated one at a time from the adjacent well strip 111 for sample analysis in the automated sample analyzer.

Figure 6:
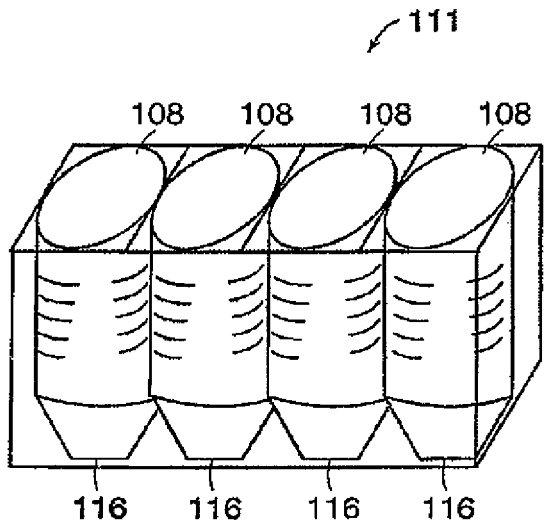
FIG. 6 is a perspective view of a well strip with cylindrically shaped wells.

A sample well 108 can have a variety of shapes. For example, in one embodiment of a well 108, the inside dimension of sample well 108 is rectangular as shown in FIG. 1. In other embodiments, the inside dimension of well 108 is cylindrical as shown in FIG. 6, or funnel-shaped as shown in FIG. 7.

Figure 7:
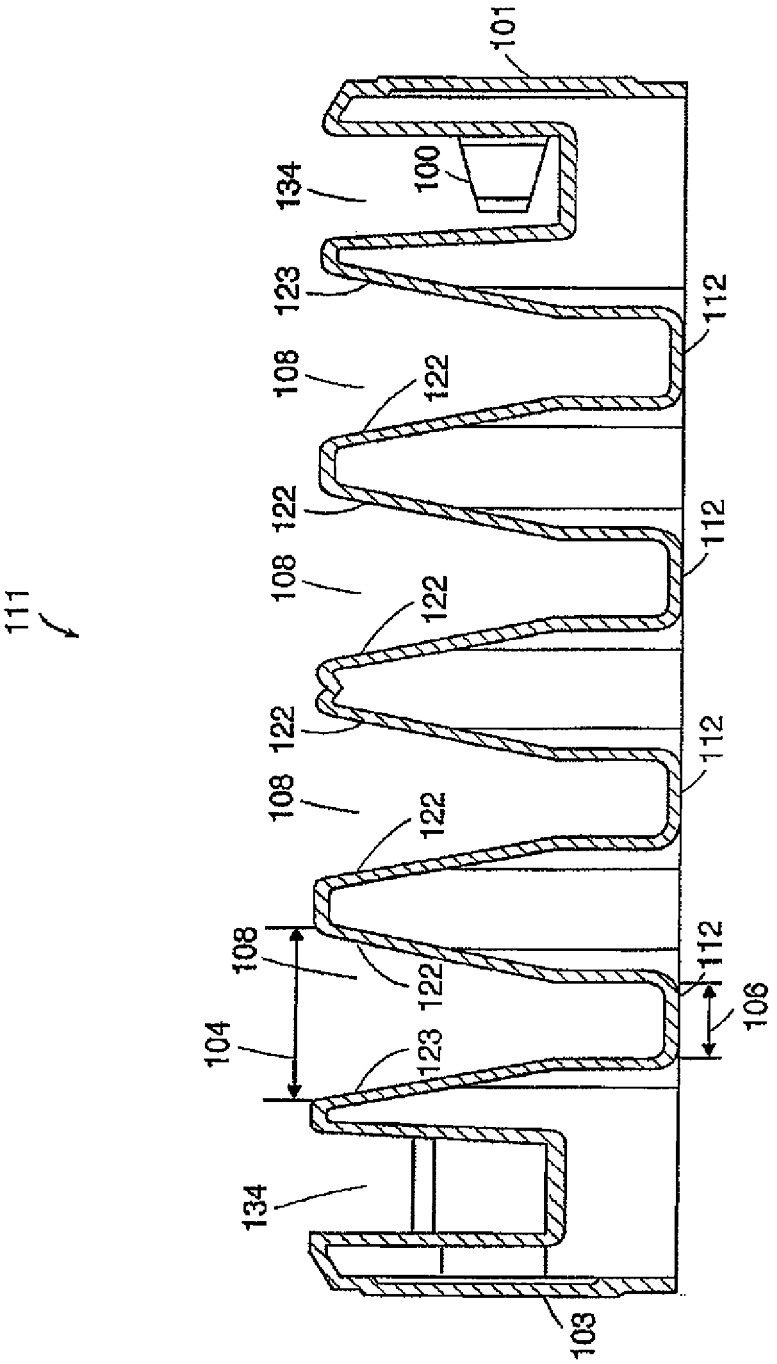
FIG. 7 is a sectional view of a well strip with funnel-shaped wells.

In a preferred embodiment of the invention, well 108, as shown in FIG. 7, is substantially funnel-shaped with a substantially flat-bottomed base 112. The funnel-shape geometry of the well narrows from the top portion of the well 108, where sample and reagents are added to the well, to the bottom portion, thereby minimizing the sample volume necessary to run an analysis of the sample. The volume of sample required is only that volume of sample that will fill the volume of the well 108 where optical windows 116 are located. Therefore, typically, only a small amount of fluid sample, in the range of 25-500 micro-liters, preferably 150 micro-liters, is needed for an assay.

Other well shapes are possible and the shape of the well is not limited to the embodiments illustrated. The well can be any shape as long as there is substantially no optical distortion of the wall of well 108 where the optical window 116 is located.

A sample well 108, illustrated in FIG. 1, in one embodiment, has an open top 113, a base 112, and four walls including a first side wall 121*a* and a second side wall 124*a*. First wall 121*a* and second wall 124*a* have a top portion substantially adjacent to the top 113 and a bottom portion substantially adjacent to the base 112. In one embodiment, the bottom portion of the first wall 121*a* and second wall 124*a* includes an optical window 116.

Figure 8:
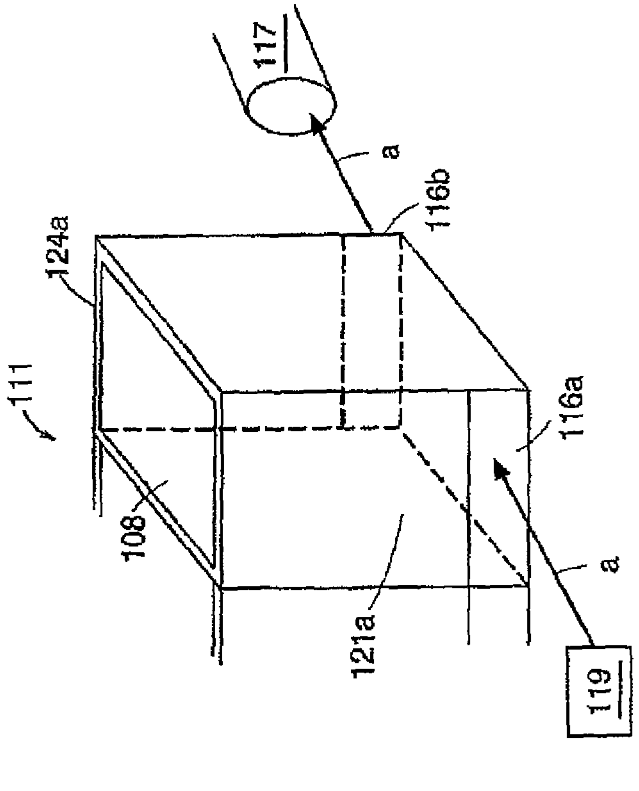
FIG. 8 is a perspective view of a portion of a well strip and a light transmission path through a sample.

For analysis by an optical reader in an automated analytical instrument, for example, illustrated in FIG. 8, the bottom portion of the first wall 121*a* and second wall 124*a* of the well 108 have optical windows 116*a* and 116*b* located on opposing bottom portions of the well 108. Optical windows 116*a* and 116*b* allow transmission of light of one or more wavelengths from a source 119 substantially along the direction of arrow (a) through the first optical window 116*a*, through the sample, through the second optical window 116*b*, and then to an optical detector 117 positioned on the opposite side of the well 108, to obtain an optical reading of the sample. An optical window may be needed to maximize transmission of light of a specific wavelength from its source 119 through the sample to the optical detector 117 if the walls of the sample well 108 are otherwise substantially non-transmissive of that wavelength, Preferably the optical windows allow the light from the source 119 to pass through the optical windows 116*a*, 116*b* with minimal or insubstantial distortion. The optical windows 116*a*, 116*b* preferably have optically clear and flat surfaces.

Figure 9:
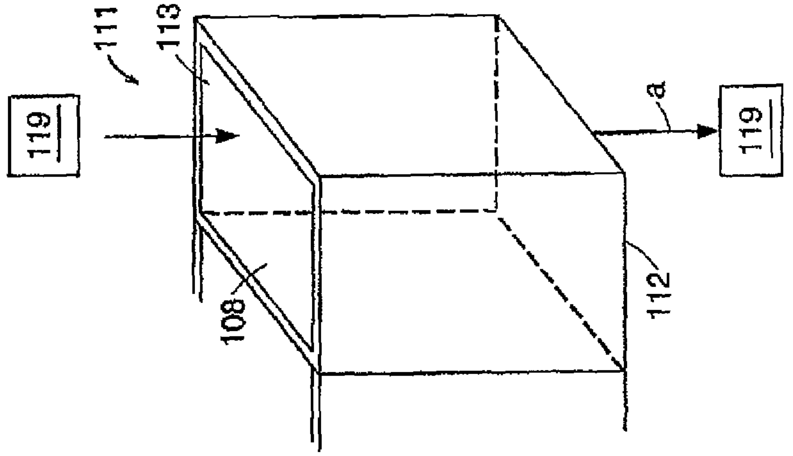
FIG. 9 is a perspective view of a portion of a well strip and a light transmission path through a sample.

The location of the optical window 116 on the well 108 is not limited to that depicted in FIG. 8. Referring to FIG. 9, for example, in one embodiment, the optical window 116 is located in the base 112 of the wells 108 and the source 119 of the transmitted light (a) is located above the top 113 of the well 108. The transmitted light for sample analysis passes through the sample, through the optical window in the base 112, to the detector 117 positioned as illustrated in FIG. 9 below the base 112. Alternatively, the transmitted light may pass in the opposite direction, with the source of transmitted light below the base 112 of the well 108, the transmitted light passing through the optical window in the base 112, through the sample, and finally through the top 113 of the well 108 where the detector 117 is positioned (not shown). In yet another embodiment, the source 119 of light may be located at the top 113 or bottom 112 of well 108 and the detector 117 may be located at the side of well 108. In these embodiments, multiple well strips attached to each other can be subjected to analysis.

Figure 10:
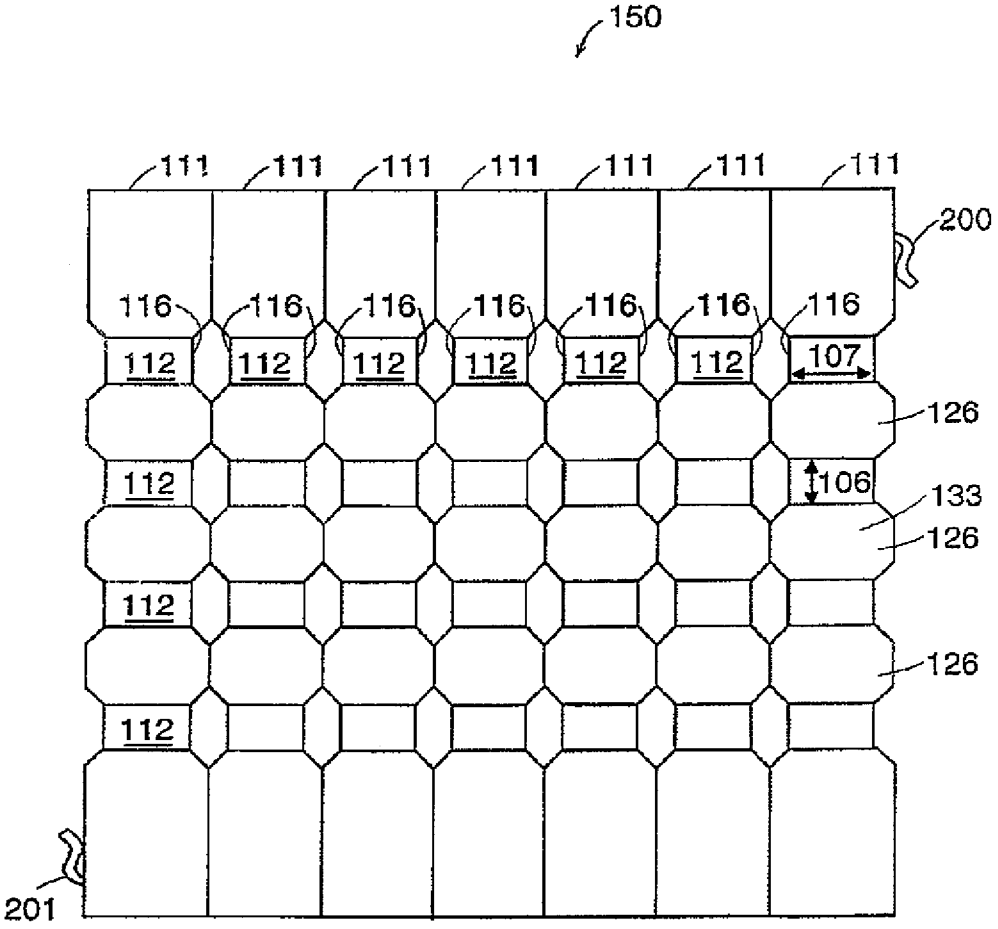
FIG. 10 is a bottom view of a sample holder system.

The funnel-shaped wells provide an additional important feature of one aspect of the invention. In one embodiment, illustrated from the bottom of a sample holder system 150 in FIG. 10, the base 112 of each well in a well strip 111 is spaced apart from the base 112 of the adjacent well in an adjacent well strip 111, while the well strips are oriented parallel to one another. Thus, the funnel-shaped wells prevent optical windows 116 located in the bottom portion of each well 108 from rubbing against the bottom portion of the corresponding well 108 in the adjacent well strip 111 when the well strips 111 are arranged side-by-side. When optical windows 116 are located in the bottom portion of the well 108, the funnel-shape prevents optical windows 116 of adjacent well strips 111 aligned side-by-side, from scratching or otherwise damaging the optical window 116 of an adjacent well strip 111, thereby altering the optical characteristics of the windows.

While the various embodiments of the present invention have been illustrated, it is within the scope of the present invention to have a sample holder comprising a well strip with a different number of wells, various well shapes and interlocking devices to allow a multiple arrays of well strips to be loaded onto an instrument such as automated sample analyzer. Variations and modifications of what is described herein will occur to those of ordinary skill in the art without departing from the spirit and the scope of the invention as claimed. Accordingly, the invention is to be defined not by the preceding illustrative description but instead by the spirit and scope of the following claims

What is claimed is:

1. A sample holder system for an automated sample analyzer, comprising:

at least a first well strip and a second well strip, wherein said first and second well strips are of substantially similar configuration, and each well strip comprises a first end, a second end, a longitudinal axis extending from said first end to said second end, first and second side walls, each of said walls parallel to said longitudinal axis, a plurality of wells extending in a linear arrangement along said longitudinal axis, each of said wells capable of holding a fluid sample, said first well strip comprising a first engagement piece and a second engagement piece wherein the first engagement piece is unlike said second engagement piece, said first and second engagement pieces being disposed on the same side wall of the first well strip, said second well strip comprising another first engagement piece and another second engagement piece, wherein said another first engagement piece is unlike said another second engagement piece, said another first and said another second engagement piece being disposed on the same side wall of the second well strip, wherein each of said first engagement piece and said another first engagement piece comprises a fixed end and a free end and said second engagement piece of said first well strip comprises a receiving component for receiving said free end of said another first engagement piece of said second well strip and said another second engagement piece of said second well strip comprises a receiving component for receiving said free end of said first engagement piece of said first well strip, and wherein said first and second well strips are reversibly engageable with each other by horizontal sliding parallel to said longitudinal axis of said well strips and by cooperative engagement of said first engagement piece of the first well strip with the another second engagement piece of the second well strip and cooperative engagement of said second engagement piece of the first well strip with the another first engagement piece of the second well strip.

2. The sample holder system of claim 1, wherein said first engagement piece of said first well strip is positioned substantially adjacent the first end of the first well strip, the second engagement piece of said first well strip is positioned substantially adjacent the second end of said first well strip, and said second engagement piece of said second well strip is positioned substantially adjacent the first end of said second well strip.

3. The sample holder system of claim 1, wherein said first engagement piece and said second engagement piece of said first well strip are positioned on a first side wall of said first well strip and said second engagement piece of said second well strip is positioned on a second side wall of said second well strip.

4. The sample holder system of claim 1, further comprising a first engagement piece of said second well strip substantially similar to the first engagement piece of the first well strip positioned on a same side wall as the second engagement piece of the second well strip.

5. The sample holder system of claim 1, wherein said first engagement piece comprises a flange.

6. The sample holder system of claim 1, wherein said wells each comprise an optical window.

* * * * *